United States Patent [19]

Pasini et al.

[11] Patent Number: 5,145,848
[45] Date of Patent: Sep. 8, 1992

[54] AMINO ANTHRACENEDIONES-BIS PLATINUM COMPLEXES, USEFUL AS ANTITUMORAL AGENTS

[75] Inventors: Alessandro Pasini; Franco Zunino; Odoardo Tofanetti; Carmelo A. Gandolfi; Sergio Tognella; Silvano Spinelli, all of Milan, Italy

[73] Assignee: Boehringer Biochemia Robin S.p.A., Milan, Italy

[21] Appl. No.: 499,405

[22] PCT Filed: Dec. 7, 1988

[86] PCT No.: PCT/EP88/01110
§ 371 Date: Jun. 14, 1990
§ 102(e) Date: Jun. 14, 1990

[87] PCT Pub. No.: WO89/05815
PCT Pub. Date: Jun. 29, 1989

[30] Foreign Application Priority Data

Dec. 18, 1987 [IT] Italy ................. 23094 A/87
Oct. 26, 1988 [IT] Italy ................. 48492 A/88

[51] Int. Cl.$^5$ .............. A01N 55/02; A61K 31/555
[52] U.S. Cl. ........................ 514/185; 544/64; 546/10; 552/209; 556/136; 556/137
[58] Field of Search ............ 556/136, 137; 552/209; 514/185; 544/64; 546/10

[56] References Cited

U.S. PATENT DOCUMENTS 4,732,893 9/1991 Pasini et al. ................. 556/137

FOREIGN PATENT DOCUMENTS 0037486 10/1981 European Pat. Off. .
0170290 2/1986 European Pat. Off. .

OTHER PUBLICATIONS

Gibson et al., J. Med. Chem. 1991, 34, 414–420.

*Primary Examiner*—Jose G. Dees
*Assistant Examiner*—Joseph M. Conrad, III
*Attorney, Agent, or Firm*—Nikaido, Marmelstein, Murray & Oram

[57] ABSTRACT

Compounds of the formula:

$$(Solv)_n\text{-}(XX'Pt)\diagup^{NH_2Rb}_{\diagdown NHRa\text{-}(CH_2)_n\text{-}A\text{-}} \quad (I)$$

$$\diagup^{RbNH_2}_{\text{-}(CH_2)_n\text{-}NHRa}(Pt\ XX').(Solv)_n$$

are disclosed, such as 1,4-bis[2(3,6,9-trioxa)undecylamino-ethylamino]-5,8-dihydroxy anthraquinone 2HCl.

These compounds exhibit antineoplastic activity and can be used to treat tumors.

10 Claims, No Drawings

AMINO ANTHRACENEDIONES-BIS PLATINUM COMPLEXES, USEFUL AS ANTITUMORAL AGENTS

This invention concerns new bis-platinum complexes, a method for their preparation and pharmaceutical compositions containing them.

An object of this invention is bis-cis-platinum complexes of formula I:

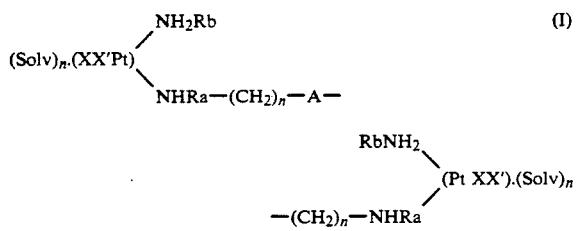

wherein
- X, X', that can be the same or different, are ligands selected from the group consisting of Cl, Br, OH, $CH_3SOCH_3 \cdot Cl$, $CH_3SOCH_3 \cdot Br$, $CH_3SOCH_3 \cdot OH$ or, taken together, from the anion of a linear or cyclic, optionally substituted, dicarboxylic acid;
- n is zero, 0.5 or an integer from 1 to 5;
- Solv is a solvent of crystallization selected from the group of water, $C_1$–$C_5$-alcohols, acetonitrile and ethylacetate;
- A is a disubstituted 1,4-anthracenedione of formula:

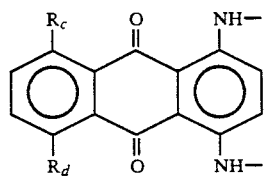

wherein each of Rc and Rd, that can be the same or different, are hydrogen or hydroxy;

Rb is either a linear or branched $C_1$–$C_6$ alkyl residue optionally substituted by hydroxy, $C_1$—$C_3$-alkoxy, $C_2$–$C_8$-polyalkoxy or sulphonic groups, or it represents a residue of a mono-amino-sugar, in acetalic or linear form of formulae a and b respectively:

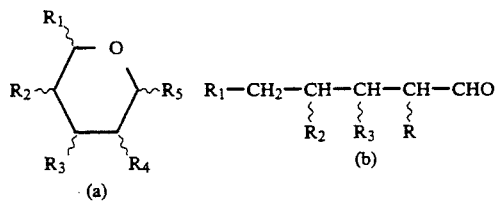

' wherein $R_1$ is hydrogen, $C_1$–$C_3$-alkyl, hydroxymethyl or aminomethyl group, $R_2$, $R_3$ and $R_4$ are amino, hydroxy or hydrogen with the proviso that at least one of them is hydrogen and only one of $R_1$, $R_2$ or $R_3$ be an amino group, $R_5$ is hydroxy, $C_1$–$C_3$-alkoxy or benzlyoxy; when $R_5$ is hydroxy, the formulae a and b represent the same structure wherein the cyclic hemiacetalic form and the opened aldehydic form are in equilibrium, whereas when $R_5$ is alkoxy or benzlyoxy, it may be either an $\alpha$ or a $\beta$-oloside;

Ra is hydrogen, $C_1$–$C_5$-alkyl, —$(CH_2CH_2O)_pH$, $(CH_2CH_2O)_pOCH_3$, $(CH_2CH_2O)_pCH_2H_5$;

n is an integer from 2 to 3 and p is an integer from 1 to 6;

and salts of said complexes with non-toxic and pharmaceutically acceptable acids.

Pharmaceutically useful salts of compound I are those with inorganic acids, as hydrohalogenidric acids, e.g. hydrochloric, hydrobromic and hydroiodic acids; or with organic acids such as acetic, succinic, tartaric and fumaric acids.

Examples of preferred aminosugars as ligands of the compounds of the invention are: 2-amino-desoxy-D-glucose(D-glucosamine), α-D-xylo-pyranosylamine, α-D-lyxo-piranoxylamine, α-D-manno-pyranosylamine, α-D-ribo-pyranosylamine, 1-daunosamine, 1-acosamine, 1-ristosamine, 2-amino-2-desoxy-D-galactose (galactosamine, D-chondrosamine), α-D-arabino-pyranosylamine, 6-amino-6-deoxy-α-D-glucopyranose, 2-amino-2,6-dideoxy-L-glucose, 3-amino-3-deoxy-D-glucose, 2-amino-2,6-dideoxy-D-glucose, 3-amino-3,6-dideo-D-mannose (mycosamine).

The compounds of the invention are obtained by mixing the solution of an anthracenedione ligand II:

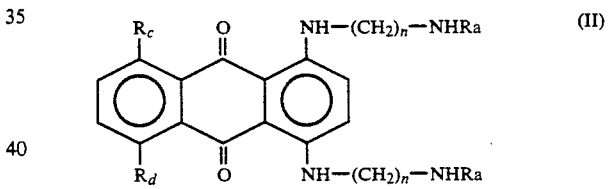

either as a free base or as a salt, wherein Ra, Rc, Rd and n have the above meanings, in a suitable solvent, with at least 2 molar equivalents of a platinum complex III

wherein $M^{(+)}$ is a cation, e.g. a cation of an alkaline metal or a quaternary phosphonium salt, X" is an univalent anion, preferably halogen (chlorine, bromine, iodine) and Rb is an alkyl residue of an amine or of an amino sugar as above described, dissolved in a suitable solvent, so giving rise to the formation of the compounds Ia:

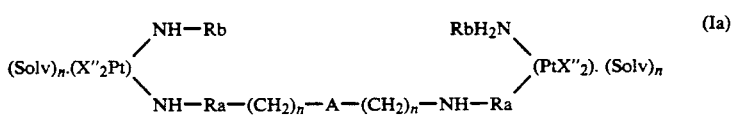

wherein Solv, X", Ra, Rb, n, A have the above meanings.

Compounds Ia may be optionally reacted with water in suitable medium to obtain compounds Ib:

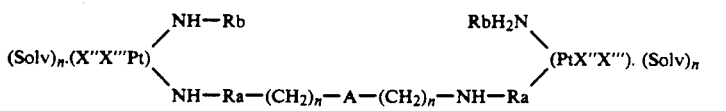

$$\underset{NH-Ra-(CH_2)_n-A-(CH_2)_n-NH-Ra}{(Solv)_n \cdot (X''X'''Pt) \diagup \overset{NH-Rb}{\diagdown}} \qquad \underset{}{\overset{RbH_2N}{\diagdown} \diagup (PtX''X''') \cdot (Solv)_n} \qquad (Ib)$$

wherein Solv, X'', Ra, Rb, n, A are as above defined and X''' is hydroxy; finally, if desired, said compounds Ia, Ib are reacted with dimethylsulphoxide to give other compounds of the invention.

Said compounds may also be treated with alkali, earth-alkali or silver salts of dicarboxylic acids such as malonic or succinic acids, optionally substituted, to give the compounds I wherein X and X', taken together, form the anion of dicarboxylic acid such as malonate, hydroxymalonate, 1,2-cyclohexanedicarboxylate, etc.

When the ligand is a salt, the compounds of the invention are also salts that, if desired, can be converted into neutral complexes by treatment with equimolar quantities of a base.

If desired, neutral complexes of formula I can be converted into the corresponding slats by reaction with stoichiometric quantities of non-toxic pharmaceutically acceptable acids.

Preferred solvents for the preparation of the reagent are water, mono- or polyhydroxylic $C_1$-$C_4$-alcohols particularly ethanol, ethylene glycols, polyglycols, acetonitrile, dimethylformamide, formamide, dimethylacetamide and mixtures thereof. Solutions of ligands and reagents are preferably mixed at temperatures ranging from $-10°$ C. to $40°-50°$ C., preferably from $-5°$ C. to room temperature.

Reaction times range from a few minutes to several days, but usually do not exceed 8 hours and periods lasting from a few minutes to 2-3 hours are often sufficient to complete the reaction.

Aquo-complexes of formula Ib are obtained from complexes Ia, and their formation occurs by slow exchange of labile Cl with ligand OH, following to a prolonged treatment with water or aqueous solutions of compounds of formula Ia.

Aquo-complexes are then obtained from aqueous solutions of compounds IB, by precipitation, preferably with low molecular weight alcohols.

Whereas only some of the complexes Ia and Ib are provided with high solubility in water, all the complexes of Ia and Ib are characterized by a remarkable solubility in dimethylsulphoxide (DMSO). Immediate dilution with water of these solutions yields stable water solutions of the compounds of the invention. If the solutions of complexes Ia and Ib in DMSO are kept for a prolonged time, from 10 minutes to some days but preferably for same hours at room temperature, the introduction in the complex of a DMSO molecule coordinated to the platinum atom occurs.

Complexes of formula I wherein at least one of X is $CH_3SOCH_3 \cdot Cl$ or $CH_3SOCH_3 \cdot OH$ are isolated for instance by evaporation of DMSO or by precipitation with a suitable solvent and optional subsequent crystallization.

Evaporation of DMSO is generally carried out under vacuum and all the above reactions are preferably carried out under inert gas atmosphere. The compounds of the invention wherein the labile ligand contains one and/or two DMSO moles per platinum atom are completely hydrosoluble and do not require dimethylsulphoxide and/or dimethylformamide as co-solvents for their solubilization in water.

Preferred compounds of the invention are those wherein the anthracenedione ligand is salified at least by an equivalent of a monovalent acid, but more preferably by two equivalents of said acids.

Particularly preferred compounds have the following formulae:

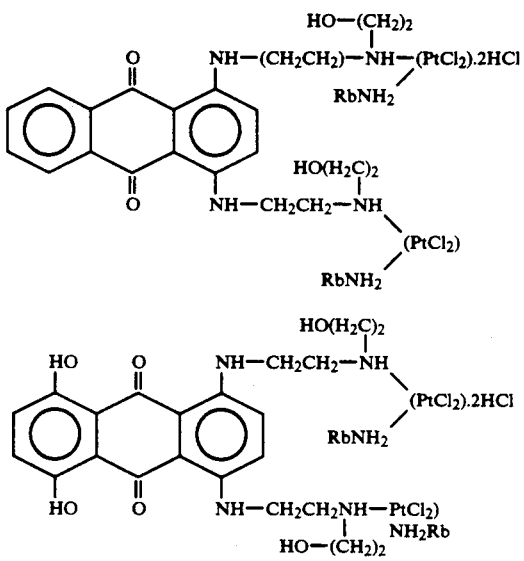

The amino anthracenediones of formula II used in the present invention are mostly known compounds and they are prepared using methods widely known in the literature, see for instance: R. K. Y. Zee-cheng et al., J. Med. Chem., 21, 291, 1978 and ibidem; 22, 501, 1979; K. C. Murdock et al. J. Med. Chem., 22, 1024, 1979; R. K. Hohnson et al., Cancer Chemotherap. Rep. 63, 425 (1970); R. K. J. Zee-cheng et al., Drugs of the future 8, 229, 1983 and cited references, U.S. Pat. No. 4,934,007.

The anthracenedione compounds of formula II wherein Ra is $(CH_2CH_2O)_pH$, $(CH_2CH_2O)_pCH_3$ or $(CH_2CH_2O)_pC_2H_5$ (p is an integer form 2 to 6) are new and are prepared in the same way as known compounds having $p_2=1$, substituting the reagent $H_2N$—$CH_2CH_2$ $NH$—$(CH_2CH_2O)_{p2}Z$ wherein Z is H, $CH_3$, $C_2H_5$ with the corresponding reagent $H_2N \cdot CH_2CH_2$— $NH$—$(CH_2CH_2O)_{p1}Z$, $p_1$, $p_2$ and Z being as above described.

The platinum complexes of general formula III $$M^{(+)}[PtX''_3H_2N-Rb]^{(-)} \qquad (III)$$

are prepared according to methods usual for these kinds of mono-amino-platinum-II complexes. Detailed teachings are already described for the preparation of compounds III wherein $M^+$ is $K^+$ and $Rb$-$NH_2$ is tert-butylamine (tba). For instance, the preparation of complex $K[PtCl_3tba]$ is described by E. Bersanetti et al. in Inorg. Chim. Acta, 93, 167 (1984).

More recently, other methods for the preparation of platinum aminotrichloro complexes have been described by F. D. Rochon et al, Inorg. Chem., 26, 3065, 1987 and by S. Jaworski et al., Inorg. Chim. Acta, 153, 31, 1988.

A detailed method for the preparation of aminotrichloroplatinum complexes, wherein the amino ligand is an aminosugar, is described hereinafter.

Neutral dichloroplatinum complexes of formula [Ptcl2(am)2] wherein (am) is an amino-sugar were disclosed by J. J. Hlavka et al., in U.S. Pat. No. 4,587,331 as compounds useful to induce regression and/or as palliatives in the treatment of tumors in mammals.

Examples of transformations of aminotrichloro complexes to mixed diaminodichloro complexes of formula [PtCl2(am)(am')] were reported by S. Jaworski (above cited) and by F. D. Ronchon et al., Can. J. Chem. 64, 1894, 1986. Said references do not teach however the preparation of compounds wherein a ligand at least is an amino-sugar.

The preparation of monoamino compounds wherein cation M+ is the triphenylphosphonium is described for instance by C. M. Abrams et al. Inorg. Chim. Acta 131, 3 (1987). A typical example of a compound prepared following this method is [(C6H5)4P][PtCl3-(NH3)].

Useful instructions for the preparation of said phosphonium complexes are also described by F. D. Rochon et al. Inorg. Chem. 26, 3065(1987), allowing an easier isolation technique. The efficiency of platinum II and IV compounds as anti-tumor agents, and particularly that of amino-platinum II complexes have been described by Rosenberg (B. Rosenberg et al. Nature 205, 965, 1965).

The antineoplastic activity of said complexes has been proved in several tumor bearing animals. These compounds inhibit tumors such as ascitic leukaemia, Walker 256 carcinosarcoma, mammary tumors induced by dimethylbenzanthracene and ascitic melanoma B-16. Among these compounds cis-diaminodichloroplatinum II (CDDP) is the most studied and it has now entered in the clinical practice. Other platinum II complexes have also been successfully experimented in animals, see for example "Platinum, gold and other metal chemotherapeutic agents; chemistry and biochemistry"; S. J. Lippard Ed., A.C.S. Symp. Series, 209 Washington D.C. (1983).

Cis platinum compounds currently used correspond to complexes of general formula:

wherein A is a carrier ligand, usually an aminic nitrogen residue. Said ligand can be monodentate (NH3, R-NH2, R-NH-R) or bidentate, e.g. 1,2-diaminoethane, while X is a leaving group which can also be monodentate (e.g. Cl—) or bidentate, e.g.

-continued

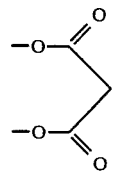

As shown in "Platinum complexes: a new class of antineoplastic agents" from F. R. M. Leh and W. Wolf, J. Pharmac. Sc. 65, 315, 1976, the function of the carrier ligand is of influencing the activity of the complex conferring to it particular steric and electronic characteristics and determining the basicity of the molecule, while on the leaving groups depends the use of hydrolysis of the complex, and then its survival in biological liquids. In other words, the leaving group should influence the possibility of the compound to reach the site of action, where selective release occurs.

On the other hand, it is accepted that the carrier ligand is likely to be permanently bound to the platinum atom in the site of action (see Caradonna et al., "Platinum coordination complexes" page 914, M. P. Hacher et al., M. Nijhoff Publ., Boston, 1984).

In the case of CDDP, its activity is displayed in the treatment of genito-urinary tumors, head and neck tumor and osteosarcoma. Clinical observation confirms the efficacy of the compound in a number of human tumors, and often in combination with other chemotherapeutic agents. Due to serious gastro-intestinal, renal side effects, hematologic and neurologic complications (ototoxicity) there is an increase in chemical work, with the aim of preparing new derivatives provided with better therapeutical index and a wider spectrum of action.

With this purpose, cis platinum complexes have been described wherein the leaving group is formed by chelating systems for platinum atom, like those present in a polycyclic quinone, having an hydroxy group in peri position in a ring fused with the quinone ring

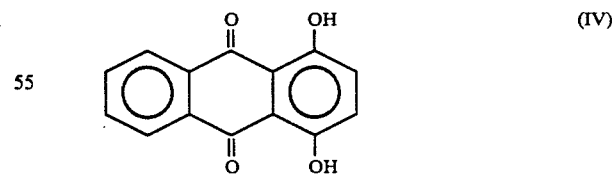

or by other hydroxyketonic chelating systems, such as for instance those disclosed in U.S. Pat. No. 4,283,342.

Other examples of this kind of compounds are described in U.S. Pat. Nos. 3,876,675 and 4,588,836.

More particularly U.S. Pat. No. 4,296,030 describes the preparation of numerous 1,4-bis(amino-substituted)-5,8-dihydroxyanthracenediones of general formula V:

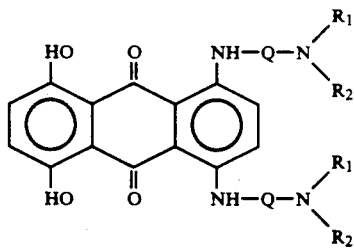

(V)

wherein $R_1$ and $R_2$ are hydrogen, $C_1$-$C_4$-alkyl or $C_2$-$C_4$-hydroxyalkyl groups and Q is a divalent alkyl residue (e.g. —$(CH_2)_n$); and n is an integer from 2 to 4, and also the preparation of their chelates with metals are iron, platinum, copper, zinc, chromium, zirconium, cobalt, palladium.

The preparation of these chelates is carried out by heating in a suitable solvent such as water, alcohols, dioxane or mixtures thereof to the reflux temperature for a period from 1 to 6 hours, a diamino-dihydroxyanthracenedione of formula V with an appropriate metal salt, which in case of platinum salts is platinum chloride or potassium tetrachloroplatinate to give compounds of formula VI:

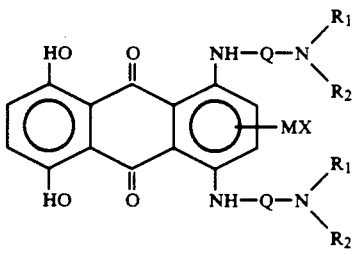

(VI)

wherein MX can be bis(platinum chloride chelate) or a tris(platinum chloride chelate).

In EP A 109732 the preparation of particular cis-platinum complexes of formula VII is disclosed:

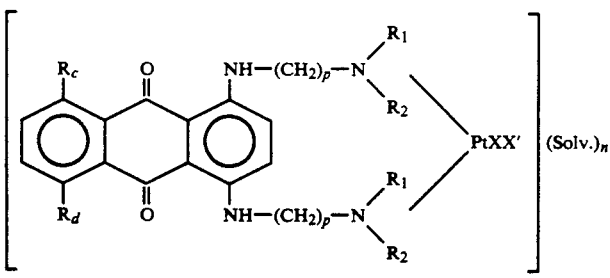

(VII)

wherein Rc, Rd, p, XX', Solv have the above described meanings and $R_1'$, $R_2'$, $R_3'$, $R_4'$ that can be the same or different, are lower hydrogen alkyl, $(CH_2)_p$—OH or taken together, form a nitrogen cyclic substituent such as morpholine, wherein platinum is not chelated to the quinone system but forms a cis-complex with the terminal N atom of the 1,4 chains.

Said preparation comprises the reaction of a solution of 1,4-diamino-dihydroxy anthracenedione with at least 1 molar equivalent of $K_2PtCl_4$ at room temperature.

The complexes of formula VII are characterized by surprisingly powerful cytotoxic effect, in comparison with other known cis-platinum complexes, this effect as shown by a long term survival of tumor bearing animals treated with the relatively higher dosages.

The high activity of compounds VII and said unexpected long term survival have been ascribed to their particular vehiculating activity, i.e. capacity to act as a "carrier" for anthracenedione ligand independently on the relevant antineoplastic activity of the latter; the "in test" activity of the molecule was then a consequence of the particular characteristics of nitrogen vector as "carrier".

In this specific case, it has been found out that the anthracenediones themselves can conveniently react with monoamino platinum complexes of formula III, that if taken alone have an almost irrelevant antineoplastic activity, to form new cis-diamino-platinum complexes, having a common anthracenedione carrier and that are able to improve long-term survival of tumor-affected animals, at very low dosages.

Comparative studies conducted on compounds of the invention, typical of which is compound (DHAQ) $(PtCl_2tba)_2 \cdot 2HCl$ (coded BBR 1939) of formula:

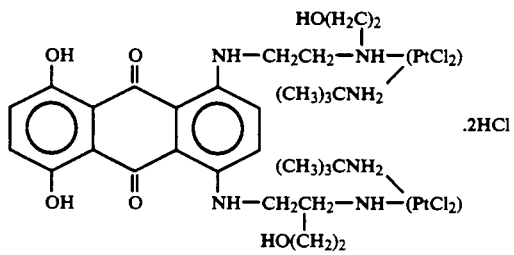

with a compound of EP109732, such as the compound coded BBR 1734, show the surprising results reached by the present invention.

For instance, compounds BBR 1734 and BBR 1939 have been compared in leukaemia $P_{388}$ in rats $CD_2F_1$, with cis-platinum and mithoxanthrone (DHAQ·2HCl) as reference compounds. $10^5$ leukaemic cells were injected at day 0 and the compounds were administered intraperitoneally the day after, defined as day 1 of the experiment.

The data, shown in Table I clearly indicate the particular activity of BBR 1939 in comparison with mithoxanthrone alone and cis-platinum.

TABLE I

| Compounds | Dosage (mg/Kg, i.p.) | MST (days) | T/C % | TOX | LTS (60 days) |
|---|---|---|---|---|---|
| BBR 1734 | — | 11–12 | 100 | 0 | 0 |
| | 37 | TOXIC | — | — | — |
| | 20 | 16 | 155 | 0/10 | 0/10 |
| | 15 | 26 | 252 | 0/10 | 3/10 |
| | 10 | 22 | 213 | 0/10 | 0/10 |
| | 7.5 | 26 | 252 | 0/10 | 1/10 |

TABLE I-continued

| Compounds | Dosage (mg/Kg, i.p.) | MST (days) | T/C % | TOX | LTS (60 days) |
|---|---|---|---|---|---|
| | 5.0 | 20 | 197 | 0/10 | 0/10 |
| BBR 1939 | 15 | TOXIC | — | — | — |
| | 10 | 36 | 300 | 1/10 | 2/10 |
| | 5 | 39 | 325 | 0/10 | 4/10 |
| | 2.5 | 26 | 216 | 0/10 | 1/10 |
| | 1.25 | 27 | 225 | 0/10 | 1/10 |
| cis-platinum | 14 | 11.5 | 99 | 2/7 | 0/7 |
| | 10 | 18.8 | 162 | 0/7 | 0/7 |
| | 6 | 22.5 | 198 | 0/7 | 0/7 |
| Mitoxan- | 25.8 | 40.5 | 368 | 1/7 | 0/7 |
| throne | 18.4 | 42.5 | 386 | 0/7 | 1/7 |
| | 11.1 | 36.5 | 331 | 0/7 | 1/7 |
| | 3.75 | 32.5 | 295 | 0/7 | 2/7 |

Furthermore, it is immediately evident that low dosages such as 1.25 mg/kg of BBR 1939 allowed to obtain an higher survival of animals than the monoplatinum complex BBR 1734, whereas at four times higher dosages T/C % values of 325 were reached.

The particular importance of the compounds of the invention is evidenced by results obtained in some forms of experimental leukaemic neoplasiae resistant to cis-platinum, e.g. L1210/CDDP leukaemia.

Once again, dosages of about 5 mg/kg allowed to obtain T/C% values of 324. The data are reported in Table II.

TABLE II

Effect of BBR 1939 on leukaemia[a] L1210/CDDP on rats CD$_2$Fl Comparison with CDDP

| Compounds | Dosage (mg/Kg, i.p.) | MST (days) | T/C % | TOX | LTS (60 days) |
|---|---|---|---|---|---|
| Controls | — | 11.4 | 100 | — | — |
| BBR 1939 | 10 | 37 | 324 | 0/10 | 1/10 |
| | 5. | 37 | 324 | 0/10 | 4/10 |
| | 2.5 | 18 | 157 | 0/10 | 3/10 |
| CDDP | 12.5 | 9.3 | 103 | 1/10 | 0/10 |
| | 7.5 | 11.6 | 101 | 0/10 | 0/10 |
| | 5. | 11.1 | 97 | 0/10 | 0/10 |

[a]10$^5$ cell/rat injected i.p. at day "0"
Compounds were administered at day "1"

The compounds of the invention are thus considered particularly useful for the treatment of neoplasiae that are resistant to treatment with cis-platinum complexes, and in particular to cis-diamino-dichloro-platinum (cDDP). In vitro comparative studies with cDDP further confirm the particular efficacy of the compounds of the invention.

Table II shows some experimental data obtained "in vitro" with respect to other leukaemic forms such as human erythroleukosis K562, as a further proof of the wide spectrum of action of the compounds of the invention and of their high efficacy compared with cis-platinum.

TABLE III

Effect of BBR 1939 on in vitro growth[b] of murine leukaemia[a] L1210/CDDP and human erythroleukosis K562 b - Comparison with CDDP:

| Cell line | Drug | Dose ug/ml | IC %[c] 24 | After hours 48 | 72 |
|---|---|---|---|---|---|
| L1210/CDDP | BBR 1939 | 0.1 | 65 | 90 | 98 |
| | | 0.05 | 61 | 88 | 97 |
| | | 0.01 | 48 | 78 | 94 |
| | | 0.005 | 48 | 66 | 87 |
| | | 0.001 | 23 | 17 | 53 |
| | CDDP | 50 | 80 | 99 | 100 |
| | | 10 | 78 | 92 | 86 |
| | | 5 | 54 | 87 | 84 |

TABLE III-continued

Effect of BBR 1939 on in vitro growth[b] of murine leukaemia[a] L1210/CDDP and human erythroleukosis K562 b - Comparison with CDDP:

| Cell line | Drug | Dose ug/ml | IC %[c] 24 | After hours 48 | 72 |
|---|---|---|---|---|---|
| | | 1 | 30 | 18 | 44 |
| | | 0.5 | 20 | 8 | 37 |
| K562 | BBR 1939 | 0.1 | 50 | 72 | 84 |
| | | 0.5 | 37 | 66 | 78 |
| | | 0.01 | 28 | 41 | 44 |
| | | 0.005 | 10 | 23 | 26 |
| | CDDP | 100 | 56 | 85 | 91 |
| | | 50 | 52 | 85 | 91 |
| | | 10 | 35 | 76 | 87 |
| | | 5 | 28 | 71 | 82 |
| | | 1 | 22 | 52 | 54 |

[a]10$^5$ cells were plated in triplicate at time "0"
[b]means used: RPMI 1640 + 10 Y FCS (inactivated in warm) + 2-mercaptoethanol 10$^{-3}$M
[c]IC %: inhibition percentage of cellular growth (treated animals against controls)

The results of said experiments further confirm the activity of the compounds of this invention; moreover their efficacy seems to have no correlation with their toxicity.

The compounds of the invention wherein Rb is the residue of an aminosugar exhibit an higher hydrophylic character which results in enhanced pharmacological properties.

The compounds of the invention are deemed effective in man when administered at dosages ranging from about 0.05 mg to about 200 mg per m$^2$ of body surface per day. The dosage of active principle for a patient weighing 70 kg ranges from 0.4 mg to about 420 mg, administered in a 24 hour period.

This schedule can be established individually, in order to allow an optimal therapeutical result.

So, for instance, the dosage can be administered daily in subdivided parts, while the exact dosage depends obviously on age, weight and overall patient's conditions and the above dosages can be reduced as a consequence of the particular therapeutical situation.

The active principle can also be administered by intravenous, intramuscular, subcutaneous or intraperitoneal route.

A therapeutical dosage can also be administered at alternate days and/or at 2 consecutive days followed by 2, 3 or more days without treatment.

It is also possible to administer the compounds orally, at dosages at least 3–10 times higher than that by parenteral route.

The compounds of the invention can also be administered in experimental protocols of polychemotherapy in combination with other antineoplastic drugs, such as antracyclines, cyclophosphamide, bleomycine, vinblastine.

They can also be used in combination with GSH in accordance with BE 904,717 and Italian Patent Application No. 21925 A/86 of 7.10.1986.

Pharmaceutical and veterinary compositions containing compounds of the invention must be prepared with the normal care used for the preparation of pharmaceutical compositions containing cis-platinum derivatives and include diluents and conventional supports.

For instance, for intravenous administrations infusions, intramuscular and subcutaneous injections, isotonic aqueous solutions and respectively sterile solutions or suspensions in aqueous or non-aqueous vehicles are used, and they are preferably prepared immediately before use starting from lyophilized products prepared conventionally and containing the active principles of the invention. The invention is further illustrated but not limited by the following examples.

EXAMPLE 1

A solution of 27 g of 2[(3,6,9-trioxa)undecyl)amino]-ethylamine in 50 ml of N, N,N', N'-tetramethylethylenediamine is deareated by argon-bubbling for 20 minutes. 10.2 g of leuco-1,4,5,8-tetrahydroxyanthraquinone are added then under stirring.

The solution is then heated under an inert gas atmosphere to 50°-52° C. under constant stirring for 4 hours, then it is allowed to cool at room temperature. The separated crystalline solid, which is dark red, is filtered and washed with cold ethanol to give 17.5 g of leuco-1,4-bis[2(3,6,9-trioxa)-undecyl-amino-ethyl-amino]-5,6-dihydroxyanthraquinone. This compound is refluxed for 20 minutes in 200 ml nitrobenzene and the hot solution is filtered. The filtrate is heated to the boiling point and, after cooling, the precipitated solid is filtered and washed with ethanol to give 10.42 g of 1,4-bis[2(3,6,9-trioxa)undecylamino-ethylamino]-5,6-dihydroxyanthraquinone.

A solution of compound (1.2 g) in 2-methoxyethanol is added with an excess of 8 N HCl in 2-methoxyethanol and, after cooling at 0°-5° C., the separated crystalline compound is filtered, to give 1,4-bis[2(3,6,9-trioxa)-undecylamino-ethylamino]-5,6-dihydroxyanthraquinone 2HCl.

EXAMPLE 2

Using in the procedure of Example 1 a leuco-1,4-dihydroxy-anthraquinone, 1,4-bis[2(3,6,9-trioxa)-undecylamino-ethylamino]anthraquinone is prepared.

EXAMPLE 3

Using the following amines in the procedure of examples 1-2: 2(11-hydroxy-3,6,9-trioxa-undecylamino)ethylamine and 2(11-methoxy-3,6,9-trioxa-undecylamino)ethylamine, the following compounds were prepared: 1,4-bis[2-(11-hydroxy-3,6,9-trioxa-undecylamino)ethylamino]-5,8dihydroxy anthraquinone·2HCl; 1,4-bis[2-(11-hydroxy-3,6,9-trioxa-undecylamino)ethylamino]-anthraquinone·2HCl.

EXAMPLE 4

A solution of 1,4-bis[2-(hydroxyethylamino)ethylamino]-5,8dihydroxy-anthraquinone·2HCl (0.27 mmoles) in 20 ml water is added, with stirring and in the dark, to a solution of K[PtCl$_3$t-butylamine] 264 mg (0.64 mmoles) in 20 ml deionized water. Addition is performed in 15 minutes. A crystalline precipitate begins to separate.

Precipitation is completed in two hours. The crystalline precipitate is filtered, washed with ethanol, diethyl ether and dried under vacuum to give 160 mg of the bis-diamino-platinum complex: bis(cis-tert-butylamine-dichloro-platinum)-N,N-1,4-bis[2-(hydroxyethylamino)ethylamino)]-5,8-dihydroxy-anthraquinone ·2HCl·H$_2$O, found % 29.95, H, 4.44; N, 6.90; Pt, 31.1; Cl, 16.9.
calc. % 29.7, H, 4.45; N, 6.92; Pt, 32.1; Cl, 17.5.
C$_{30}$H$_{54}$N$_6$O$_7$Pt$_2$Cl$_6$ IR 1609, 1561 cm$^{-1}$hydroxyquinone structure: 325, 307 cm$^{-1}$ bond stretchings Pt-Cl typical for a cis-PtCl$_2$ structure.

EXAMPLE 5

Using in the procedure of Example 4, 219.4 mg of complex K[Pt-Cl$_3$-t-butylamine] and respectively 184 mg of 1,4-bis[2-hydroxyethylamino)ethylamino]-anthraquinone, 140 mg of bis(cis-tert-butylamine-dichloro-platinum)-N,N-1,4-bis[2-hydroxyethylamino)-ethylamino]anthraquinone·2HCl·H$_2$O.:
C$_{30}$H$_{54}$N$_6$O$_5$Pt$_2$Cl$_6$ found % C, 30.5; H, 4.57; N, 7.02; Pt, 32.2; Cl, 17.5.
calc. % C, 30.46; H, 4.57; N, 7.11; Pt, 33.0; Cl, 18.0.
IR 1595 cm$^{-1}$quinone; 325, 305 cm$^{-1}$ Pt-Cl are obtained.

EXAMPLE 6

By substituting an anthraquinone prepared in accordance with examples 1,2,3,4,5, the following bis-diaminoplatinum complexes were obtained:

bis-(cis-tert-butylamine-dichloro-platinum)-N,N-{1,4-bis[2-(3,6,9-trioxa-undecylamino)-ethylamino]-5,8dihydroxyanthraquinone}·2HCl·H$_2$O.;

bis-(cis-tert-butylamine-dichloro-platinum)-N,N-{1,4-bis[2-(3,6,9-trioxa-undecylamino)-ethylamino]-anthraquinone} bis-(cis-tert-butylamine-dichloro-platinum)-N,N-{1,4-bis[2-(11-hydroxy-3,6,9-undecylamino)-ethylamino]-anthraquinone}·2HCl·H$_2$O.;

bis-(cis-tert-butylamine-dichloro-platinum)-N,N-{1,4-bis[2-(11-methoxy-3,6-trioxa-undecylamino)-ethylamino]-5,8-dihydroxyanthraquinone}·2HCl·H$_2$O.;

bis-(cis-tert-butylamine-dichloro-platinum)-N,N-{1,4-bis[2-(11-hydroxy-3,6,9-trioxa-undecylamino)-ethylamino]-5,8-dihydoxyanthraquinone}·2HCl·H$_2$O.

EXAMPLE 7

A bis-(aminediiopdoplatinum) [PtI$_2$NH$_2$R$_b$]$_2$, e.g. [PtI$_2$(H$_2$N—CH$_2$CH$_2$OH)]$_2$ (0.99 g) is suspended in a solution of 1.01 g of silver nitrate in 15 ml of deionized water and kept away from light.

The mixture is stirred in the dark for two days at room temperature. It is then filtered on celite, and 0.6 g of potassium chloride are added to the clear solution of an aquo-nitrate platinum ethanolamine complex.

The mixture is then stirred in the dark and at room temperature for 20 hours and filtered.

By adding to the solution an excess of tetraphenyl-phosphonium chloride, a crystalline precipitate of tetraphenylphosphonium [hydroxyethylaminetrichloroplatinum]-[(C$_6$H$_5$)$_3$P]$^+$ [PtCl$_3$—(H$_2$N—(CH$_2$)$_2$—OH)], C$_{26}$H$_{27}$NCl$_3$OPPt, is obtained.

found % C, 44.55; H, 3.75; N, 1.93; Cl, 15.38.
calc. % C, 44.47; H, 3.85; N, 2.00; Cl, 15.18.

EXAMPLE 8

Using in the procedure of Example 7 a suitable bis-diamine-diiodo-platinum complex wherein the amino bond is selected in the group of 3-hydroxypropylamine, 1,1-dimethyl-2-hydroxyethylamine and trihydroxymethamine, the following platinum complexes were obtained:

tetraphenylphosphonium[trichloro-3-hydroxymethyl-propylamine-platinate];
tetraphenylphosphonium[trichloro-1,1-dimethyl-2-hydroxyethylamine-platinate];

tetraphenylphosphonium[trichloro-trihydroxymethyl-methaneamine-platinate].

EXAMPLE 9

A solution of 450 mg of tetraphenylphosphonium[trichloro-hydroxyethyl-amine-platinate] (0.64 mmoles) in acetone is added slowly and under stirring to a solution of 1,4-bis[2-(hydroxyethylamino)ethylamino]-5,8-dihydroxyantrhaquinone·2HCl (150 mg; 0.27 mmoles) in 20 ml water. It is kept under stirring in the dark for 24 hours, then filtered and the solution is diluted with acetone for ⅓ of its volume. After 2 hours under stirring, it is filtered and the filtrate is then diluted with 6 volumes of acetone.

It is left to rest for 12 hours at 5°–0° C. A crystalline precipitate (80 mg) of bis-(dichloro(2-hydroxyethyl-amine-platinum)]-N,N-1,4-bis[2-hydroxyethylamino)-ethylamino]-5,8dihydroxyanthraquinone is obtained.

Using in the same procedure the tetraphenylphosphonium salts prepared in accordance with Example 8, the following bis(diamino-dichloro-platinum complexes) were obtained:
bis-(hydroxypropylamine-dichloro-platinum)-N,N-{1,4-bis[2-hydroxyethylamino)-ethylamino]-5,8dihydroxyanthraquinone};
bis-(1,1-dimethyl-2-hydroxyethylamine-dichloro-platinum)-N,N-{1,4-bis[2-hydroxyethylamino)-ethylamino]-5,8dihydroxyanthraquinone};
bis-(trihydroxymethylmethamine-dichloro-platinum)-N,N-{1,4-bis[2-hydroxyethylamino)-ethylamino]-5,8dihydroxyanthraquinone}.

EXAMPLE 10

D(+)-glucosamine HCl (0.43 g 2 mmoles) and $K_2CO_3$ (0.138 g, 1 mmole) are added to a suspension of $K_2PtCl_4$ (0.83 g, 2 mmoles) in dimethylformamide (60 ml) previously deareated, in an inert gas atmosphere and under stirring. The reaction mixture is heated for 7 hours at 60°00 C. under inert atmosphere and then concentrated under reduced pressure up to a volume of 5 ml. The inorganic precipitate is centrifugated and filtered; the clear solution is diluted with an hexane-ethyl acetate mixture (3/1, v/v; 20 ml) to allow the separation of an oily mass.

After decantation of the surnatant, the oily mass is treated with 3×20 ml of the hexane-ethylacetate mixture in order to remove dimethylformamide. The residual yellow oil is dried under vacuo and then crystallized from ethanol.

0.89 g of potassium D(+) trichloro-glucosamine-platinate are obtained.

Calc. for K[PtCl$_3$ (glucosamine)]½ DMF
($C_{7.5}H_{16.5}N_{1.5}O_{5.5}PtCl_3K$)
$C_{16.2}H_{3.0}N_{3.8}$
Found % $C_{16.4}H_{3.2}N_{3.8}$
Pt-Cl: 328, 325, 320 cm$^{-1}$ (KBk)

The compound is a uni-univalent electrolyte in aqueous solution.

m=98 ohm$^{-1}$ cm$^2$ mole$^{-1}$ for C=10$^{-3}$ M/liter.

EXAMPLE 11

By substituting in the procedure of Example 10, the D(+)-glucosamine with an amino sugar selected in the group of 3-amino-3-deoxy-glucose, 1-daunosamine, 1-acosamine, 1-ristosamine, 6-amino-6-desoxy-α-D-glucopyranose, α-D-arabino-pyranosylamine, galactosamine, α-D-manno-pyranosylamine, 2-amino-2,6-dideoxy-D-glucose, mycosamine, α-D-ribopiranosylamine, α-D-xylo-pyranosylamine and of α-D-lixo-pyranosylamine, the following complexes are prepared:
potassium-trichloro-N-(3-amino-3-deoxy-glucose)-platinate,
potassium-trichloro-1-daunosamine-platinate,
potassium-trichloro-1-acosamine-platinate,
potassium-trichloro-1-ritosamine-platinate,
potassium-trichloro-N-(6-amine-6-desoxy-α-D-glycopyranose)-platinate,
potassium-trichloro-N-(α-D-arabino-pyranosylamine)-platinate,
potassium-trichloro-N-(galactosamine)-platinate,
potassium-trichloro-N-(α-D-manno-pyranosylamine)-platinate,
potassium-trichloro-N-(2-amine-2,6-dideoxy-D-glucose)-platinate, or
potassium-trichloro-N-(6-desoxy--glucosamine)-platinate,
potassium-trichloro-N-(mycosamine)-platinate,
potassium-trichloro-N-(α-D-ribo-pyranosylamine)-platinate,
potassium-trichloro-N-(α-D-xilo-pyranosylamine)-platinate,
potassium-trichloro-N-(α-lixo-pyranosylamine)-platinate.

EXAMPLE 12

A solution of 1,4-bis-[2-(hydroxyethylamino)e-thylamino]-anthracene-9,10-dione·2HCl (0.24 g, 0.5 mmoli) in water (20 ml) is slowly added to a solution of potassium trichloro-D(+)-glucosamine-platinate. ½ DMF (0.56 g, 1 mmole) in 20 ml of water in inert gas atmosphere and under stirring. The mixture, after being kept for 18 hours at room temperature in inert gas atmosphere, is evaporated to dryness under reduced pressure. The residual mass is then extracted with a methanol/chloroform mixture (4/1 vv, 30 ml), filtered and diluted with an excess of diethyl ether.

A crystalline solid precipitate which is filtered and dried under vacuo to obtain 0.62 g of bis-[cis-dichloro-D(+)-glucosamine-platinum]-N,N-1,4-bis[2(hydroxyethylamino)ethylamino]anthracene-9,10dione·2HCl H$_2$O.

Pt-Cl 320–315 cm$^{-1}$
found % C, 29.8; H, 4.3; N, 5.9; Cl, 15.1. calc. for $C_{34}H_{56}N_6O_{14}Pt_2Cl_6$:
C, 29.7; H, 4.1; N, 16.1; Cl, 15.5.

EXAMPLE 13

A solution of 0.256 g of 1,4-bis[2-(hydroxyethylamino)ethylamino]-5,8dihydroxy-anthracene-9,10-dione in water (20 ml) is added to a solution of potassium trichloro-1-daunosamine-platinate (0.49 g) in water (18 ml), in inert gas atmosphere and under stirring. The solution is allowed to stand for 24 hours, then it is evaporated under vacuo.

The residue is suspended in 10 ml of dimethylformamide and, after filtration of KCl, the solution is diluted with ethanol (40 ml).

A crystalline precipitate is obtained which is filtered to give 0.41 g of bis-[(cis-dichloro-(1)daunosamine-platinum]-N,N-1,4-bis[2-(hydroxyethylamino)e-thylamino]-5,8-dihydroxy-anthracene-9,10-dione, as a non-hydrochloride species whose structure is confirmed by the IR spectrum.

I.R.: ν(Pt-Cl) 320 e 310 cm$^{-1}$ (KBr).

EXAMPLE 14

According to the procedures of Examples 12 and 13, by reacting a potassium amino-sugar-trichloro-platinate prepared as in Examples 10 and 11 and a suitable anthracenedione, the following complexes are prepared:

bis-[cis-D(+)-glucosamine-dichloro-platinum]-N,N-1,4-bis[2-(hydroxyethylamino)ethylamino]-5,8-dihydroxy-anthracene-9,10-dione·2HCl;

bis-[cis-1-daunosamine-dichloro-platinum]-N,N-1,4-bis[2-(hydroxyethylamino)ethylamino]-5,8-dihydroxy-anthracene-9,10-dione·2HCl;

bis-[cis-(6-amino-6deoxy-α-glucosamine-dichloro-platinum]-N,N-1,4-bis[2-(hydroxyethylamino)ethylamino]-5,8-dihydroxy-anthracene-9,10-dione·2HCl;

bis-[cis-(6-amino-6deoxy-α-glucopyranose)dichloro-platinum]-N,N-1,4-bis[2-(hydroxyethylamino)ethylamino]anthracene-9,10-dione·2HCl;

bis-[cis-(3-amino-3deoxy-glucose)dichloro-platinum]-N,N-1,4-bis[2-(hydroxyethylamino)ethylamino]-anthracene-9,10-dione·2HCl;

bis-[cis-(3-amino-3deoxy-glucose)dichloro-platinum]-N,N-1,4-bis[2-(hydroxyethylamino)ethylamino]-5,8-dihydroxy-anthracene-9,10-dione·2HCl;

bis-[cis-(α-D-arabino-pyranosylamine)dichloro-platinum]-N,N-1,4-bis[2-(hydroxyethylamino)ethylamino]-5,8-dihydroxy-anthracene-9,10-dione·2HCl;

bis-[cis-(α-D-arabino-pyranosylamine)dichloro-platinum]-N,N-1,4-bis[2-(hydroxyethylamino)ethylamino]-anthracene-9,10-dione·2HCl;

bis-[cis-(galactosamine)dichloro-platinum]-N,N-1,4-bis[2-(hydroxyethylamino)ethylamino]-anthracene-9,10-dione·2HCl;

bis-[cis-(1-acosamine)dichloro-platinum]-N,N-1,4-bis[2-(hydroxyethylamino)ethylamino]-anthracene-9,10-dione·2HCl;

bis-[cis-(1-acosamine)dichloro-platinum]-N,N-1,4-bis[2-(hydroxyethylamino)ethylamino]-5,8-dihydroxy-anthracene-9,10-dione·2HCl;

bis-[cis-(1-ristosamine)dichloro-platinum]-N,N-1,4-bis[2-(hydroxyethylamino)ethylamino]-anthracene-9,10-dione·2HCl;

bis-[cis-(1-ristosamine)dichloro-platinum]-N,N-1,4-bis[2-(hydroxyethylamino)ethylamino]-5,8-dihydroxy-anthracene-9,10-dione·2HCl;

bis-[cis-(α-D-manno-pyranosylamine)dichloro-platinum]-N,N-1,4-bis[2-(hydroxyethylamino)ethylamino]-anthracene-9,10-dione·2HCl;

bis-[cis-(α-D-manno-pyranosylamine)dichloro-platinum]-N,N-1,4-bis[2-(hydroxyethylamino)ethylamino]-5,8-dihydroxy-anthracene-9,10-dione·2HCl;

bis-[cis-(mycosamine)dichloro-platinum]-N,N-1,4-bis[2-(hydroxyethylamino)ethylamino]-anthracene-9,10-dione·2HCl;

bis-[cis-(mycosamine)dichloro-platinum]-N,N-1,4-bis[2-(hydroxyethylamino)ethylamino]-5,8-dihydroxy-anthracene-9,10-dione·2HCl, and their non-hydrochloride species.

EXAMPLE 15

According to each one of the previous examples, the following compounds were prepared:

bis-[cis-(6-deoxy-glucosamine)dichloro-platinum]-N,N-1,4-bis[2-amino-ethylamino]-anthracene-9,10-dione·2HCl;

bis-[cis-(6-deoxy-glucosamine)-dichloro-platinum]-N,N-1,4-bis[2-(hydroxyethylamino)ethylamino]-5,8-dihydroxy-anthracene-9,10-dione·2HCl;

bis-[cis-(α-D-lixo-pyranosylamine)-dichloro-platinum]-N,N-1,4-bis[2-ethylamino)ethylamino]-anthracene-9,10-dione·2HCl;

bis-[cis-(α-D-xylo-pyranosylamine)dichloro-platinum]-N,N-1,4-bis[2-(hydroxyethylamino)ethylamino]-5,8-dihydroxy-anthracene-9,10-dione·2HCl;

bis-[cis-(α-D-ribo-pyranosylamine)-dichloro-platinum]-N,N-1,4-bis[2-isopropylaminoethylamino]-anthracene-9,10-dione·2HCl;

bis-[cis-(α-D-ribo-pyranosylamine)-dichloro-platinum]-N,N-1,4-bis[2-(hydroxyethylamino)ethylamino]-5,8-dihydroxy-anthracene-9,10-dione·2HCl, and their non-hydrochloride species.

EXAMPLE 16

0.044 g of disodium malonate (0.30 ml) dissolved in the minimum amount of water, are added to a solution of 0.20 g of bis-[cis-glucosamine-dichloroplatinum]-N,N-1,4-bis[2-(hydroxyethylamino)ethylamino]-anthracene-9,10-dione (0.15 mmol) in 40 ml of DMF. The mixture is heated to 40° C. for 4 hours in inert atmosphere, concentrated under vacuo and filtered. After addition of ether, 0.17 g of bis-[glucosaminemalonate-platinum]-N,N-1,4-bis[2-(hydroxyethylamino)ethylamino]-anthracene-9,10-dione are obtained.

Analysis: C, 34.9; H, 2.2; N, 6.4; Pt, 28.1.

Calc. for $C_{40}H_{58}N_6O_{22}Pt_2$: C, 35.2; H, 2.1; N, 6.2; Pt 28.6.

EXAMPLE 17

According to the procedure of the previous example, by treating bis-[cis-tert-butylamine-dichloro-platinum]-N,N-1,4-bis[2-(hydroxyethylamino)ethylamino]-5,8-dihydroxy-anthraquinone, with sodium bicarbonate and then, after filtration and re-dissolution in DMF, with the disodium salt of succinic acid, bis-[tert-butylaminosuccinate-platinum]-N,N-bis[2-(hydroxyethylamino)ethylamino]-5,8-dihydroxy-anthraquinone is obtained.

We claim:

1. Compounds of formula I:

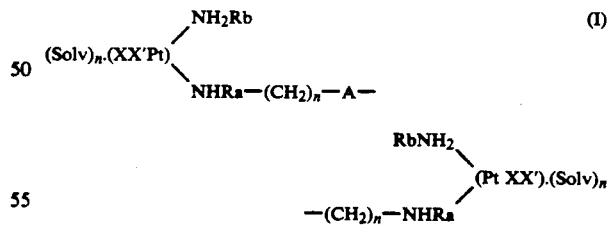

wherein
X, X', that can be the same or different, are ligands selected from the group consisting of Cl, Br, OH, $CH_3SOCH_3$·Cl, $CH_3SOCH_3$·Br, $CH_3SOCH_3$·OH or, taken together, form the anion of a linear or cyclic, optionally substituted, dicarboxylic acid;
n is zero, 0.5 or an integer from 1 to 5;
Solv is a solvent of crystallization selected from the group consisting of water, $C_1$-$C_5$-alcohols, acetonitrile and ethylacetate;
A is a disubstituted 1,4-anthracenedione of formula:

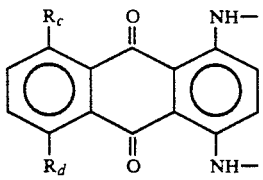

wherein each of Rc and Rd, that can be the same or different, are hydrogen or hydroxy;

Rb is either a linear or branched $C_1$–$C_6$alkyl residue optionally substituted by hydroxy, $C_1$—$C_3$-alkoxy, $C_2$–$C_8$-polyalkoxy or sulphonic groups, or it represents a residue of a mono-amino-sugar, in acetalic or linear form of formulae a and b respectively:

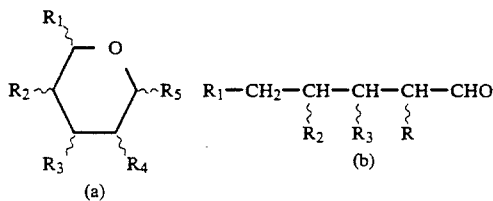

wherein $R_1$ is hydrogen, $C_1$–$C_3$-alkyl, hydroxymethyl or aminomethyl group, $R_2$, $R_3$ and $R_4$ are amino, hydroxy or hydrogen with the proviso that at least one of them is hydrogen and only one of $R_1$, $R_2$ or $R_3$ be an amino group, $R_5$ is hydroxy, $C_1$–$C_3$-alkoxy or benzlyoxy;

when $R_5$ is hydroxy, the formulae a and b represent the same structure wherein the cyclic hemiacetalic form and the opened aldehydic form are in equilibrium, whereas when $R_5$ is alkoxy or benzlyóxy, it may be either an α or a β-oloside;

Ra is hydrogen, $C_1$–$C_5$-alkyl, —$(CH_2CH_2O)_pH$, $(CH_2CH_2O)_pOCH_3$, $(CH_2CH_2O)_pCH_2H_5$;

n is an integer from 2 to 3 and p is an integer from 1 to 6;

and salts of said complexes with non-toxic and pharmaceutically acceptable acids.

2. Compounds according to claim 1, wherein Rc and Rd are hydrogen.

3. Compounds according to claim 1, wherein Rc and Rd are hydroxy.

4. Compounds according to anyone of claims 1-3, wherein X and X' are both chlorine.

5. Compounds according to anyone of claims 1-3, wherein n is 2.

6. Compounds according to anyone of claims 1-3, wherein Rb is tert-butyl and Ra is hydroxyethyl.

7. Compounds according to anyone of claims 1-3, wherein Rb is the residue of an amino-sugar.

8. Compounds according to claim 7, wherein Rb is the residue of an amino-sugar selected in the group of 2-amino-desoxy-D-glucose(D-glucosamine), α-D-xylo-pyranosylamine, α-D-lyxo-piranoxylamine, α-D-manno-pyranosylamine, α-D-ribo-pyranosylamine, 1-daunosamine, 1-acosamine, 1-ristosamine, 2-amino-2-desoxy-D-galactose (galactosamine, D-chondrosamine), α-D-arabino-pyranosylamine, 6-amino-6-deoxy-α-D-glucopyranose, 2-amino-2,6-dideoxy-L-glucose, 3-amino-3-deoxy-D-glucose, 2-amino-2,6-dideoxy-D-glucose, 3-amino-3,6-dideoxy-D-mannose (mycosamine).

9. A process for the preparation of compounds of claim 1 by reaction of an anthracenedione of general formula II

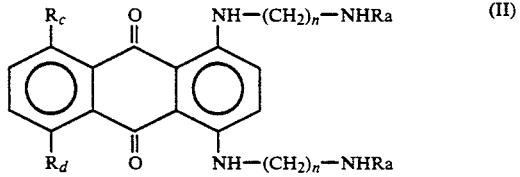

both as a free base and as a salt, wherein Ra, Rc, Rd and n have the above described meanings, in a suitable solvent, with at least two molar equivalents of a platinum complex of general formula III:

$$M^{(+)}[PtX''_3H_2N-Rb]^{(-)} \qquad (III)$$

wherein $M^{(+)}$ is a precipitating cation, X is an univalent anion, preferably a halogen (chlorine, bromine, iodine) and Rb is as above defined, dissolved in a suitable solvent, followed by crystallization and subsequent optional reactions with water of dimethylsulphoxide and/or salifications.

10. Pharmaceutical compositions having antineoplastic activity containing as an active principle a compound of claims 1-3 mixed with a suitable vehicle.

* * * * *